United States Patent [19]
Mueller et al.

[11] Patent Number: 6,110,169
[45] Date of Patent: Aug. 29, 2000

[54] CUTTING DEVICE FOR ELECTROTOMY

[75] Inventors: Gerhard Mueller; Kai Desinger, both of Berlin, Germany

[73] Assignee: Kari Desinger, Berlin, Germany

[21] Appl. No.: 09/117,874

[22] PCT Filed: Feb. 3, 1997

[86] PCT No.: PCT/DE97/00232

§ 371 Date: Aug. 7, 1998

§ 102(e) Date: Aug. 7, 1998

[87] PCT Pub. No.: WO97/28751

PCT Pub. Date: Aug. 14, 1997

[30] Foreign Application Priority Data

Feb. 7, 1996 [DE] Germany ............... 196 04 330

[51] Int. Cl.⁷ ............................................. A61B 18/18
[52] U.S. Cl. ............................ 606/48; 606/45; 606/41
[58] Field of Search .................... 606/41, 45–48, 606/50

[56] References Cited

U.S. PATENT DOCUMENTS

| | | |
|---|---|---|
| 4,074,718 | 2/1978 | Morrison . |
| 4,493,320 | 1/1985 | Treat ........................................ 606/47 |
| 4,674,499 | 6/1987 | Pao ............................................ 606/50 |
| 4,905,691 | 3/1990 | Rydell ....................................... 606/47 |
| 5,078,716 | 1/1992 | Doll ........................................... 606/47 |
| 5,318,564 | 6/1994 | Eggers ....................................... 606/47 |
| 5,445,142 | 8/1995 | Hassler, Jr. .............................. 600/105 |
| 5,836,947 | 11/1998 | Fleischman et al. ..................... 606/47 |
| 5,843,019 | 12/1998 | Eggers et al. ............................. 604/22 |

FOREIGN PATENT DOCUMENTS

| | | |
|---|---|---|
| 0453071A1 | 10/1991 | European Pat. Off. . |
| 0467501A1 | 1/1992 | European Pat. Off. . |
| 0646361A1 | 4/1995 | European Pat. Off. . |
| 0651974A2 | 10/1995 | European Pat. Off. . |

*Primary Examiner*—Michael Peffley
*Attorney, Agent, or Firm*—Venable; George H. Spencer; Allen Wood

[57] ABSTRACT

A cutting device for use in electrotomy is disclosed for use with a high frequency generator to make a cut in a cutting direction. The cutting device comprises a carrier element, and first and second electrodes each connected to the high frequency generator. Each electrode has a proximal portion attached to the carrier element and an elongated distal leg portion which terminates in a distal end. An insulation element connects the distal ends to each other with predetermined spacing between them. The elongated segments oppose each other and are aligned to be co-linear with each other along the cutting direction.

11 Claims, 5 Drawing Sheets

CUTTING DEVICE FOR ELECTROTOMY

BACKGROUND OF THE INVENTION

The invention relates to a cutting device for electrotomy.

It has long been known in surgery to use high-frequency AC current in a frequency range from 300 kHz to 2 MHz for the coagulation and separation of tissue, where the treated tissue is coagulated or vaporised; this is designated electrocoagulation or electrotomy. A differentiation must be made between monopolar and bipolar HF thermotherapy.

With monopolar HF thermotherapy, one electrode—also designated the neutral electrode—is designed as a large surface area patient outlet and is disposed near the point of intervention on the patient. The shape of the actual working electrode—also designated the active electrode—is adapted to the respective application. In this way, large surface area ball, plate or needle electrodes are used for tissue coagulation, whilst lancet or loop electrodes are used for the separation of tissue.

On the other hand, with bipolar HF thermotherapy, both electrodes are arranged directly next to the point of intervention so that the effect of the AC current is limited to the direct area of intervention which provides a high degree of safety for the patient and the user, since accidents as a result of capacitative leakage current or burning on the neutral electrode can no longer occur. A further advantage of bipolar HF thermotherapy is the significantly-reduced load resistance of the tissue between the two electrodes which reduces the required generator power whilst maintaining the thermal effect.

Furthermore, HF thermotherapy can be further subdivided according to the position of the electrodes into surface coagulation on the one hand and deep coagulation on the other hand.

With surface coagulation, two touch electrodes disposed in parallel are used with the bipolar technique, these electrodes being placed on the tissue surface, wherein the tissue which lies beneath is heated and coagulated as a result of the flow of current.

With deep coagulation, it is known to use needle, lancet or loop electrodes for monopolar electrotomy. Here, electric light arcs must be generated at the active electrode in order to vaporise tissue which lies in front of the active electrode, hence cutting the tissue. This is relatively easy with the monopolar technique, since this only requires a certain field strength to activate a sparkover at the active electrode. On the other hand, the bipolar technique places greater demand on the conception of the electrode configuration, since the physical processes in this connection are not so simple to control. In consequence, as a result of the necessary miniaturisation of the neutral electrode, bipolar electrode arrangements tend to change the electrode arrangement into different and indifferent electrodes, whereupon the functionality is effected. For this reason, only a few bipolar electrode arrangements are known for deep coagulation, such as, for example, the ball-needle arrangement for laparoscopic electrotomy and the bipolar needle electrode which, amongst others, is suitable for myomotherapy.

This known bipolar electrode arrangement comprises two needle electrodes disposed in parallel which are stuck into the tissue, whereupon the tissue lying between the electrodes is heated as a result of the current flow and is thus coagulated. However, this bipolar electrode arrangement cannot be seen as a cutting apparatus for HF surgery as a result of its dependence on monopolar dissection hooks. Furthermore, a disadvantage with the known bipolar electrode arrangement is the relatively labourious placement of the electrodes with two insertion points. Furthermore, the field distribution can only be relatively inexactly determined by the user, since the relative position of the two electrodes with regard to one another cannot usually be exactly specified.

SUMMARY OF THE INVENTION

An objective of the invention is to produce a bipolar cutting device for electrotomy, where the cutting quality and the ease of manipulation are improved with regard to known bipolar cutting apparatus.

The invention includes the technical teaching of the provision of a bipolar loop electrode for electrotomy, which is formed from the two electrodes and an insulation element arranged between the electrodes. Furthermore, the invention includes the technical teaching of replacing an electrode by an electrically-conductive fluid jet for a bipolar electrode arrangement for electrotomy, where an electromagnetic field is built up between the other electrode and the fluid jet, heating the tissue.

The cutting apparatus, according to the invention, has a bipolar electrode arrangement wherein the two electrodes are attached to a carrier element, at least on a proximally-situated part of its longitudinal extent to simplify manipulation and also for mechanical fixation. In one variation of the invention, the two electrodes are elongated and are connected to one another at their distal ends by an insulation element in order to maintain a specified electrode distance.

In the preferred embodiment of these variants, the two electrodes run together, at least at their distal ends, wherein the insulation element is arranged axially between the distal ends of the two electrodes and has an exterior cross-section which is substantially similar to the exterior cross-section of the two electrodes at their distal ends, in order to facilitate a smooth transition. Here, the bipolar electrode arrangement has a smooth and kink-free transition in the area of the insulation element, which is especially advantageous with linear cutting, with the cut being made parallel to the longitudinal axis of the electrodes.

In a further embodiment of the invention, the two electrodes each have at least two electrode limbs, angled against one another, which lie in a common plane wherein the distal electrode limbs of the two electrodes run substantially straight and coaxially towards one another, in order to permit a linear tissue cut. Hence the electrode arrangement in this version has a straight area which is formed from the distal electrode limbs and the insulation element, wherein linear cutting with a cut being made to the longitudinal axis of the electrodes is further simplified, since a linear cutting channel is formed so that fine incisions are possible.

In the preferred embodiment of the invention, the two electrodes, together with the insulation element, form a bipolar loop electrode, wherein the space between the electrodes or the electrode limbs is substantially kept free, so that apart from the linear cutting movement parallel to the plane formed by the electrodes or the electrode limbs, a cutting movement at a right angle to this is also possible.

On the other hand, in another version of the invention, the two electrodes or the electrode limbs are substantially attached by their entire length to the carrier element in order to attain high mechanical load-bearing capacity and hence smaller electrode cross-sections. Since the mechanical load-bearing capacity in these versions is almost exclusively determined by the carrier element, very small electrode cross-sections can be realised wherein the electrical power required for cutting can be drastically reduced. Furthermore, the electrodes which can be used here, with a diameter which can be less than 250 µm, offer the advantage of improved incision which is comparable to a monopolar spade electrode. Furthermore, small electrode diameters and small limb lengths allow smaller cutting radii, in an advantageous manner, which is important in surgical dissection.

In the preferred embodiment of this variant, the carrier element is designed to be spatula-shaped, wherein the proximal electrode limbs are arranged along the side edges of the carrier element and are attached to these, whilst the distal electrode limbs are arranged along the cutting edge of the spatula-shaped carrier element and are arranged on this. The insulation of the two electrodes with regard to one another can take place between the distal ends of the two distal electrode limbs or—as in the version of the invention described beforehand—by a separate insulation element or by the carrier element itself. However, it is here not necessary for the insulation element or the carrier element to completely fill the space between the distal ends of the electrodes. Rather it is decisive that the two distal ends of the electrodes are mechanically fixed to one another by the insulation element or the carrier element, which can also be facilitated by the two electrodes being connected to the carrier element along their entire length, wherein a defined air gap remains between the distal ends of the two electrodes. As a result of the increased stability and possible miniaturisation with small electrode diameters, this version of the invention is especially suitable for use in laparoscopy or in flexible endoscopy.

With the versions of the invention described above, one of the two electrodes is always the active electrode also designated the different electrode—and the other electrode is always the neutral electrode—also designated the indifferent electrode. The active electrode is distinguished by the formation of sparkovers and thus works to separate the tissue, whilst the neutral electrode merely functions as a return conductor.

In the preferred embodiment of the invention, the arrangement of an active electrode and neutral electrode can be determined by the user, whilst the cutting apparatus is so placed at the beginning of the cutting process so that one of the two electrodes touches the tissue first. This consciously-asymmetrical placement of the cutting apparatus makes that electrode which has not yet been placed the active electrode, since a significantly-larger field strength is present here as a result of the existing air gap. This air gap is then penetrated by an arc of light as a result of the great field strength so that a cushion of steam results which lifts the surrounding tissue from the active electrode, wherein sparkovers continually bridge the intermediate space between the tissue and the active electrode and palpate the entire tissue front so that the tissue is separated effectively without being touched by the active electrode. In this connection, it is important that the geometric relationships of the two electrodes—that is, for example, their effective lengths—are not too different, so that electrode assignment is not already specified by the electrode arrangement. Preferably, therefore, the two electrodes in this version of the invention have the same length in the area of the tissue contact, so that the user can freely specify the electrode assignment by means of corresponding asymmetric placement.

On the other hand, in another version of the invention, it is provided that a pre-specified electrode assignment is always set, irrespective of the operation of the cutting device by the user. Here, the two electrodes have strongly different geometries in the area of the tissue contact, especially different lengths.

On the other hand, in another version of the invention only one electrode usually touches the tissue, whereas the electrical contact between the tissue and the other electrode is effected by an electrically-conductible fluid or gas jet, which is given off by a jet in the direction of the tissue so that an electromagnetic field is formed between the one electrode and the fluid or gas jet, which heats the tissue.

Here, in order to simplify manipulation, the two electrodes are connected to a carrier element which has a hollow channel for supply of an electrically-conductible fluid, which opens into a jet-shaped opening for emission of a fluid jet. Saline solution is preferably suitable as a fluid, however the invention can also be realised by a jet of ionised gas as a fluid. It is important here that the fluid jet is contacted by the first electrode, which preferably occurs as a result of the jet-shaped opening being arranged in the first electrode. However, it is also possible that the first electrode projects into the hollow channel which serves to supply the fluid in order to make electrical contact with the fluid jet, or that it comprises a component part of this hollow channel. Furthermore, in this version it is advantageous for the function according to the invention that the jet-shaped opening is formed and arranged in such a way that the fluid jet is given off in the direction of the body tissue which is to be cut, and does not directly fall on the second electrode, otherwise the two electrodes would be short-circuited via the fluid jet. Hence, an electromagnetic field is created between the fluid jet and the second electrode, which leads to heating and at least partial vaporisation of the tissue, and hence effects cutting of the tissue.

In a preferred embodiment of this variant, the fluid jet is fanned out in a wedge shape, wherein the second electrode is extended and is arranged with its longitudinal axis coaxial to the wedge-shaped fanned fluid jet. The wedge shape of the fluid jet can be effected by suitable layout of the jet-shaped opening, however it is also possible to use several jet-shaped openings arranged about the circumference of the wedge axis, which each give off partial jets which unify to form the wedge-shaped fluid jet. Here, the second electrode can simply be designed as a needle or lancet electrode.

Other advantageous embodiments of the invention will be apparent from the following description of the preferred embodiments of the invention, by means of the figures.

DETAILED DESCRIPTION OF THE PREFERRED EMBODIMENTS

Figure 1:
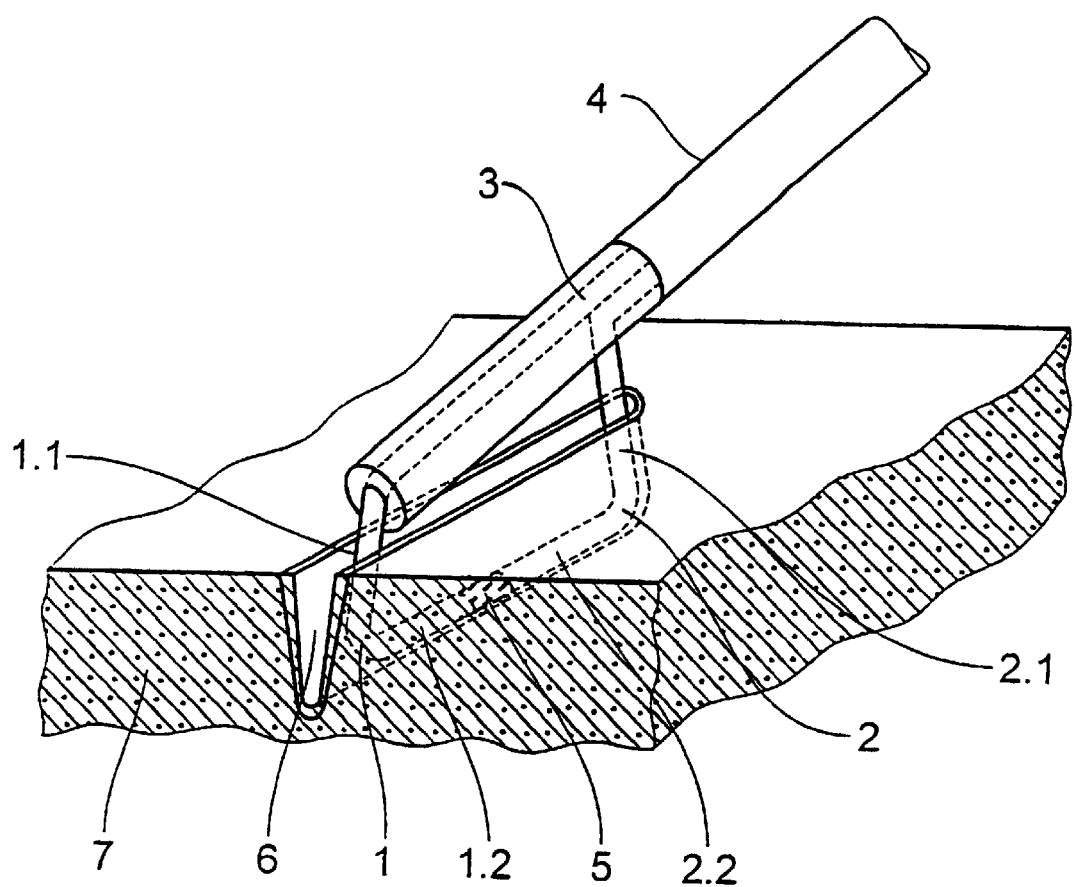
FIG. 1 As a preferred embodiment example of the invention, a cutting device for electrotomy with a bipolar loop-shaped electrode arrangement in a perspective representation, FIG. 2 The cutting device from FIG. 1 in side elevation, for explanation of the biophysical processes at the two electrodes, FIGS. 3a, 3b A further cutting device according to the invention in side elevation, and a detailed drawing of the cutting device, FIGS. 4a to 4d A cutting device for electrotomy with a replaceable cutting tip in perspective representation, and FIG. 5 A further cutting device according to the invention for electrotomy with an electrically conductible fluid jet as counter-electrode in perspective representation.

FIG. 1 shows a cutting device according to the invention for electrotomy with a bipolar electrode arrangement, which substantially comprises a first electrode 1 and a second electrode 2 of stainless steel wire, which are attached by a high temperature adhesive to a cylindrical carrier element 3 for mechanical fixing at their proximal ends, which has a formed handle 4 for manual guidance by the operator at its ends facing away from the electrodes 1, 2. The two electrodes 1, 2 are each divided into a proximal electrode limb 1.1, 2.1 and a distal electrode limb 1.2, 2.2 which is angled away from the proximal electrode limb 1.1, 2.1, wherein the individual electrode limbs 1.1, 1.2, 2.1, 2.2 of the two electrodes 1, 2 lie in a common plane and are each designed without substantial bends along their longitudinal extent. The distal electrode limbs, 1.2, 2.2, are mechanically joined to each other at their distal ends by a cylindrical insulation element 5, so that the two electrodes 1, 2, together with the insulation element 5, form a bipolar loop arrangement which permits cutting movements both parallel and at right angles to the electrode plane. However, especially advantageously, a linear cutting movement can be carried out with this cutting device, so that in this way a linear furrow-shaped incision channel 6 is formed in the tissue 7, through which the cutting device with the two distal electrode limbs 1.2, 2.2 can be pulled through.

A further advantage of the loop arrangement can be seen in that the operator retains a free view of the direct point of intervention. Moreover, the maintenance of specified electrode distances is ensured by the insulation element 5.

In order to simplify a linear cutting movement parallel to the electrode plane, the distal electrode limbs 1.2, 2.2 of the two electrodes 1, 2, together with the cylindrical insulation element 5, are arranged coaxially, wherein the insulation element 5 has the same exterior cross-section as the distal electrode limbs 1.2, 2.2 in order to attain a smooth and step-free transition between the distal electrode limbs 1.2, 2.2 and the insulation element 5.

Electrical control of the two electrodes 1, 2 takes place via separate high-frequency generators, which are each connected to the two electrodes 1, 2 via a supply line which passes through a hollow channel in the carrier element 3.

The biophysical processes during the cutting movement are clarified in the side elevation of the cutting device represented in FIG. 2, and are described in detail in the following text.

At the beginning of the cutting process, the cut is initialised, wherein assignment of the two electrodes into active electrode (different electrode) and neutral electrode (indifferent electrode) is selected by the user. To do this, the operator places the cutting device asymmetrically on the tissue 7 in such a way that the electrode 2, which is laid against the cutting direction, touches the tissue 7 first. Such a consciously-asymmetrical placement of the cutting device makes the as-yet-unplaced electrode limb 2.2 the active electrode, since here there is a substantially greater field strength as a result of the still-existing air gap. This air gap is then penetrated by an arc of light as a result of the great field strength, so that a cushion of steam 8 results which lifts the surrounding tissue 7 from the electrode 2, wherein sparkovers continually bridge the intermediate space between the tissue 7 and the active electrode 2 and touch the entire tissue front so that the tissue 7 is separated from the active electrode 2 virtually without being touched.

The cushion of steam 8 reduces in size towards the distal end of the active electrode limb 2.2, as a result of reducing sparkovers in this area. In the area of the neutral electrode limb 1.2, the tissue 7 is then pressed against the neutral electrode 1, as a result of the pressing force of the cutting device or by the reaction force of the tissue 7, which effects a good electrical contact between the tissue 7 and the neutral electrode 1, and thus a clear assignment of the current density distribution. Even with a strongly-reducing effective contact surface of the neutral electrode 1, the assignment of active and neutral electrodes remains initially intact. Only when the contact surface of the neutral electrode 1 falls below a specified minimum value can a change of the light arc and thus a change in the electrode assignment occur. For example, this case can occur when the indifferent electrode limb 1.2 is almost totally removed from the cutting channel or when the cutting speed of the cutting device is equal to zero. During normal manipulation of the represented cutting device, however, a change of the light arc cannot be observed.

Figure 2:
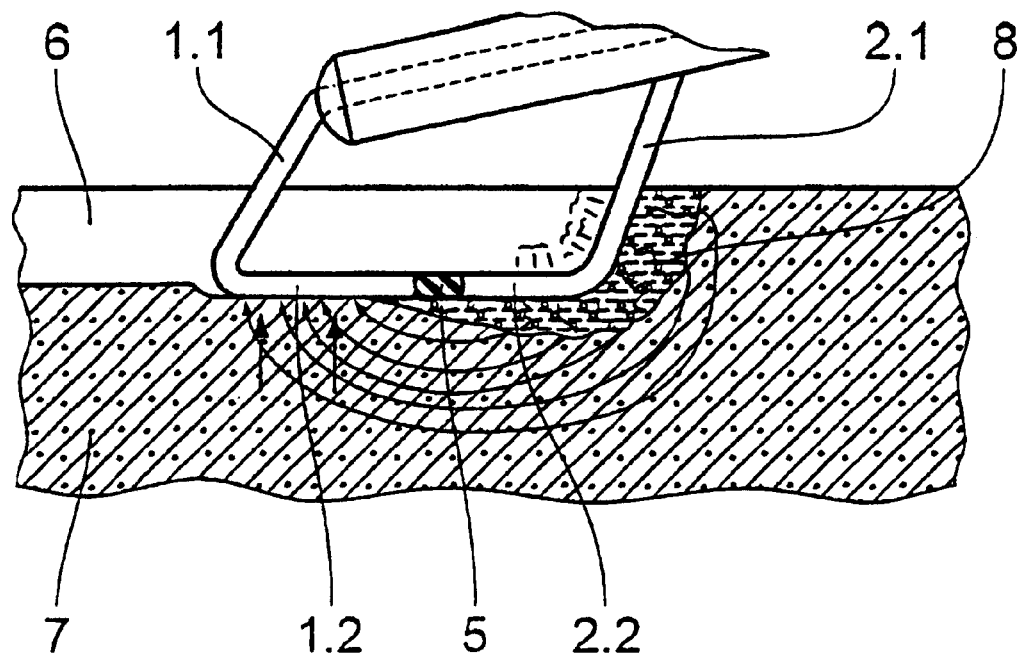
Figure 3A:
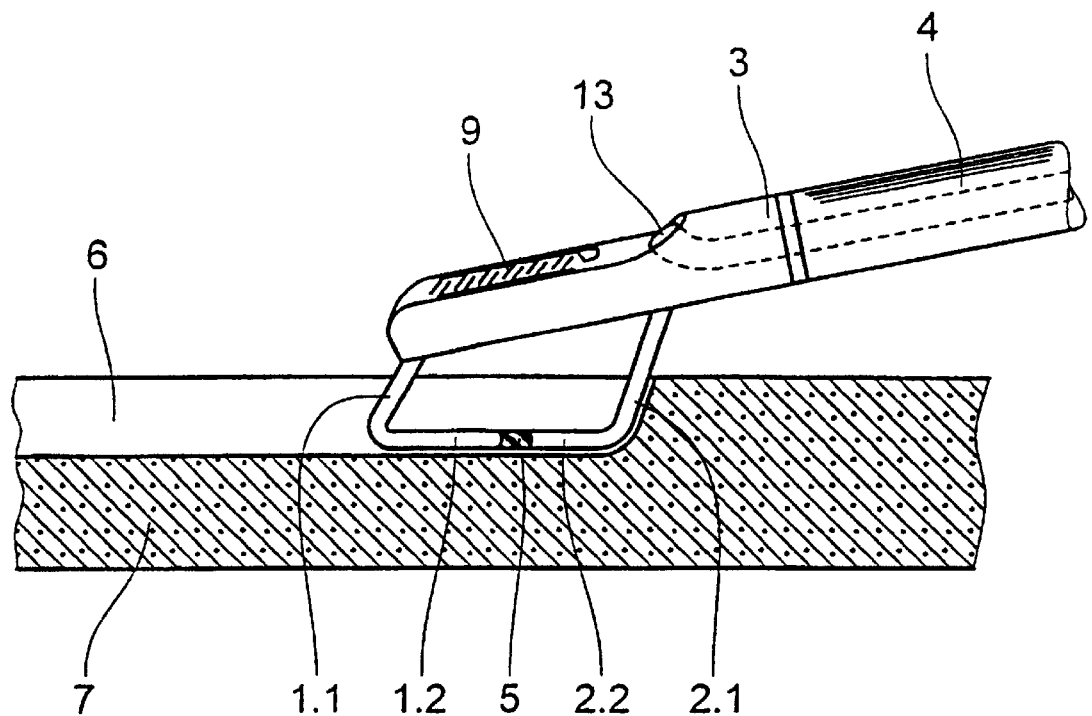
Figure 3B:
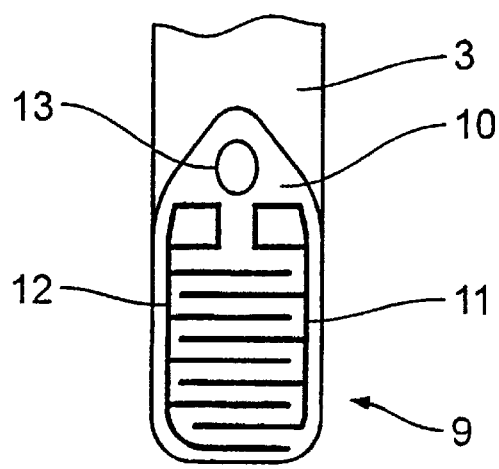

In the same way, FIG. 3a shows a cutting device for tissue separation which corresponds extensively with the hereinbefore-described cutting device, represented in FIGS. 1 and 2, but which, however, additionally has a coagulation device 9 in order to stop bleeding, which is represented in detail in FIG. 3b in top elevation. Due to the extensive constructual correspondence with the cutting device hereinbefore described, constructional elements in FIGS. 1 and 2 and also in FIGS. 3a and 3b are given the same reference characters, so that in this connection reference is made to the descriptions of the aforementioned embodiments.

The coagulation device 9 is attached on the upper side of the carrier element 3 in a recess, so that the operator must merely turn the cutting device about its longitudinal axis and place the coagulation device 9 on the tissue in order to effect electro-coagulation to stop any bleeding which occurs during tissue cutting.

In this way, it is possible to separate tissue 7 and to stop any occurring bleeding by electro-coagulation with rapid changing between the two functions. The coagulation device 9 substantially comprises a flat electrode carrier 10 of electrically insulating material and a first electrode 11 and a second electrode 12 which comprise a silver-panadium alloy, and are additionally applied and burnt onto the electrode carrier in a liquid state during manufacture via a fine jet. As a result of subsequent nickelling of the surface, the electrode material is hardened on its surface in order to give durability.

The two electrodes 11, 12 have a plurality of parallel-running line-shaped electrode tracks which interact in a meandering fashion in order to increase the effective electrode surface and to provide the most effective electro-coagulation possible.

Furthermore, the carrier element 3 is penetrated by a hollow channel to supply a rinsing fluid which opens into an opening 13 in the coagulation device 9, through which the rinsing fluid can be ejected into the tissue 7 which is to be coagulated. In this way, it is possible to prevent drying out of the tissue 7, which contributes towards an improvement in the electrical coupling of the coagulation device 9 to the tissue 7.

Figure 4A:
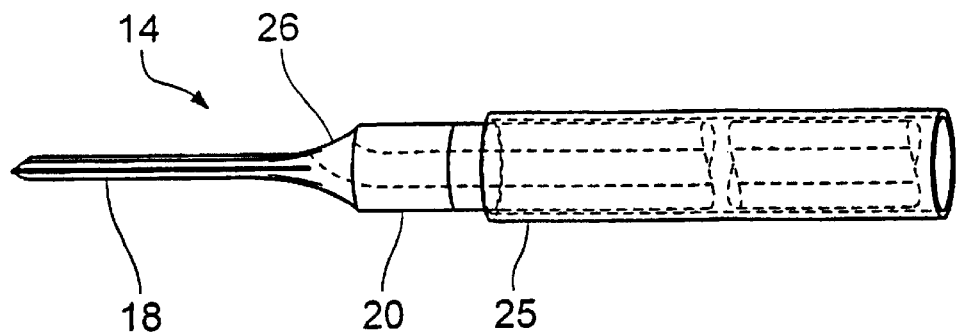
Figure 4B:
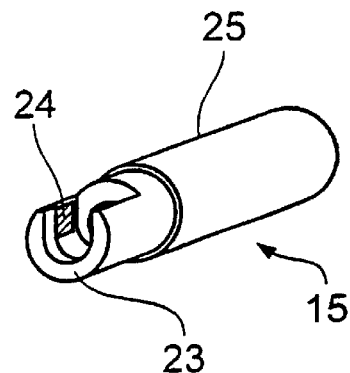
Figure 4C:
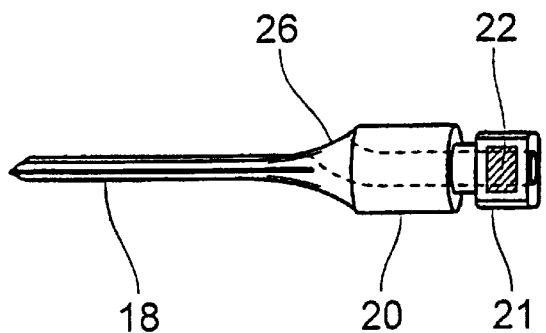
Figure 4D:
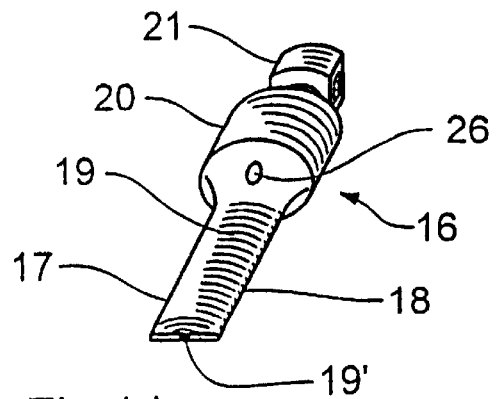

FIG. 4a shows a further cutting device 14 according to the invention for electrotomy, which substantially comprises a manipulation part 15 which is represented in FIG. 4b, and a replaceable cutting tip 16 which is shown in FIGS. 4c and 4d.

The cutting tip 16 has a first electrode 17 and a second electrode 18 for electro-thermal tissue separation, which comprise stainless steel wire with a diameter of 200 $\mu$m and which are each subdivided into a proximal electrode limb with a length of 2.5 mm and a distal electrode limb, which is angled at right angles, wherein the proximal electrode limbs are arranged along the side edges of a spatula-shaped carrier element 19 and are attached to this, whereas the distal electrode limbs are arranged along the cutting edge of the spatula-shaped carrier element 19 and are attached to this. For this, the electrodes 17, 18 are set laterally in corresponding recesses in the electrically-insulating carrier element 19, wherein the carrier element 19 fills the space between the distal ends of the two distal electrode limbs 1.2, 2.2 and forms an insulation element 19' with a pre-specified electrode distance. The carrier element 19, which comprises ceramic, here serves on the one hand for mechanical fixing and guiding of the electrodes 17, 18 and on the other hand for electrical insulation of the electrodes 17, 18 from one another.

Furthermore, the carrier element 19 has a cylindrical shaft on the side facing away from the electrodes 17, 18 on which a saddle piece 21 is formed, which allows a mechanical and electrical connection with the manipulation part 15, wherein the connection between the cutting tip 16 and the manipulation part 15 is releasable in order to allow changing of the cutting tip 16. The electrical connection of the cutting tip 16 with the manipulation part 15 is via two contact flags 22 which are connected to the two electrodes 17, 18 of the cutting tip 16.

In order to accept the cutting tip 16, the manipulation part 15 has a corresponding shape-adapted reception element 23, in which two contact flags 24 are also arranged, allowing a connection with a separate high frequency generator via supply lines, wherein the supply lines pass through a hollow channel in the manipulation part 15. Furthermore, the manipulation part 15 has a cylindrical sleeve 25 which can be pushed in an axial direction. For mounting or for replacement of the cutting tip 16, the sleeve 25 is pushed backwards to expose the reception element of the manipulation part 15. Then the saddle piece 21 of the desired cutting tip 16 is laid in the reception element 23 and the sleeve 25 is again pushed into its closed position in order to lock the connection between the cutting tip 16 and the manipulation part 15. Furthermore, the sleeve 25 can also be pushed over the cutting tip 16 in order to protect this from mechanical damage when inserted via a trochar.

Furthermore, the manipulation part 15 is penetrated by a centrally-disposed hollow channel which extends into the cutting tip 16 and which opens into an opening 26 on the upper side of the cutting tip 16. In this way, it is possible on the one hand to introduce a rinsing fluid into the tissue in order to prevent electrical drying of the tissue. On the other hand, tissue substance or fluid can be sucked out of the tissue. The axially-slideable sleeve 25 here allows, in an advantageous manner, focusing of the rinsing agent or suction stream when the sleeve is pushed over the opening 26.

Figure 5:
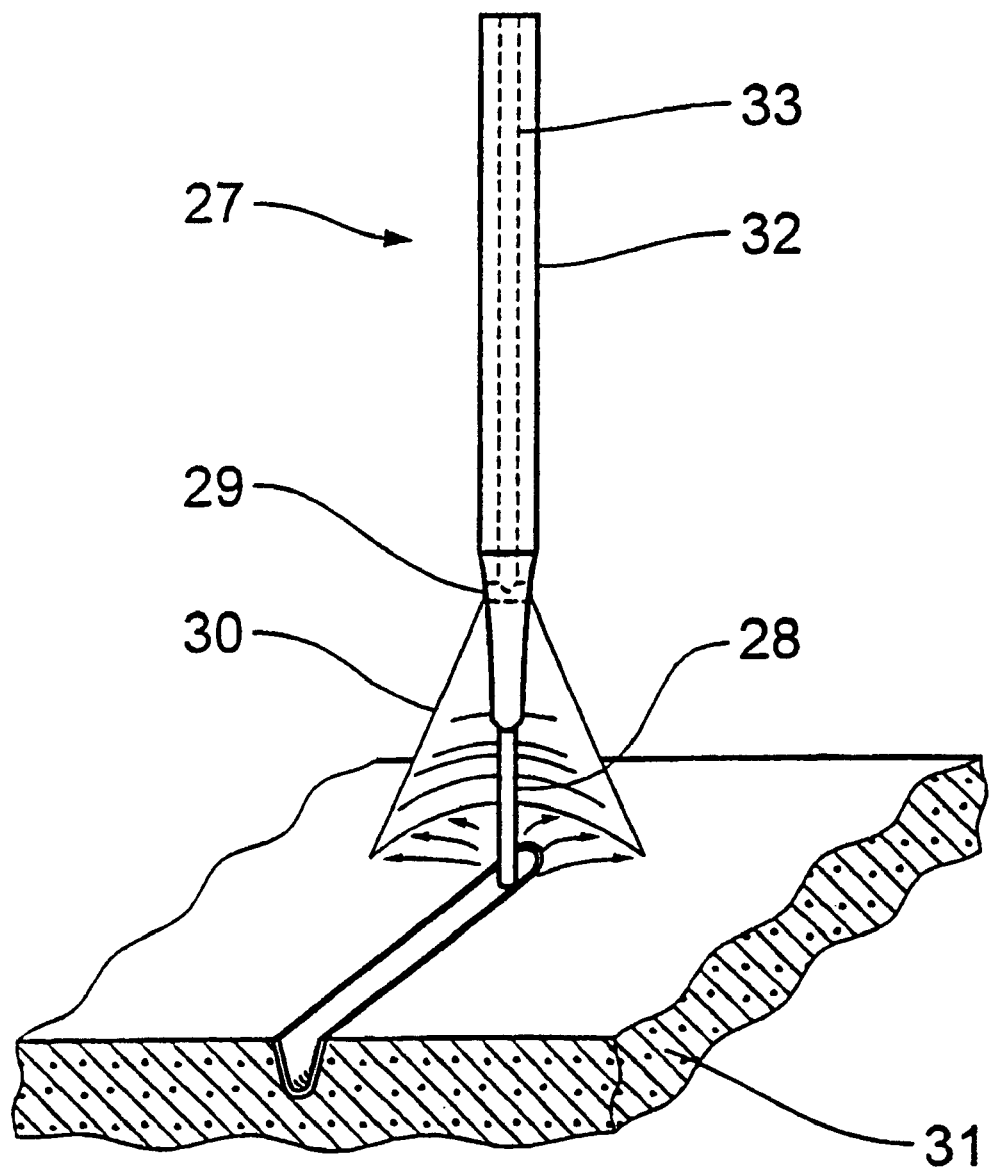

FIG. 5 shows a further cutting device 27, according to the invention, for electrotomy with a bipolar electrode arrangement with a needle electrode 28 and a ring-shaped electrode 29 which contact an electrically-conductive fluid jet 30, so that an electromagnetic field results between the fluid jet 30 and the needle electrode 28, which allows warming and separation of the tissue 31.

Here, the needle electrode 28 serves as the electrode, which is attached at its proximal end to the tip of a carrier element 32, which tapers conically in its distal area and is placed on the tissue 30 with its distal end. On the other hand, the ring-shaped electrode 29 works as the indifferent electrode, which comprises stainless steel and surrounds the conical end of the carrier element 32. For electrical contacting and supply of the electrically-conductive fluid jet 30, the ring-shaped electrode 29 has a plurality of jet-shaped openings, which are distributed about the circumference and which allow the output of the fan-shaped expanding fluid jet 30, wherein the supply of the fluid is via a hollow channel 33 running centrally in the carrier element 32 which opens into the jet-formed openings of the ring-shaped electrode 29. The ring-shaped indifferent electrode 29 thus contacts the exiting fluid jet electrically, so that the electrical circuit between the two electrodes 28, 29 is closed via the fluid jet 30 and the tissue 31.

The invention is not restricted in its embodiment to the preferred embodiment examples set out above. Rather a number of variants are conceivable which make use of the invention.

What is claimed is:

1. A cutting device for use in electrotomy with a high frequency generator to make a cut in a cutting direction, the cutting device comprising:

a carrier element;

a first electrode adapted to be connected to the high frequency generator and having a first proximal portion attached to said carrier element and a first elongated distal leg segment terminating in a first distal end;

a second electrode adapted to be connected to the high frequency generator and having a second proximal portion attached to said carrier element, and a second elongated distal leg segment terminating in a second distal end; and an insulating element connecting said first and second distal ends to each other with a predetermined spacing therebetween, wherein said first and second elongated distal leg portions oppose each other and are aligned co-linear with each other along the cutting direction, and said first and second electrodes are disposed to lie in a plane including a line along the cutting direction.

2. A cutting device according to claim 1, wherein said insulation element is arranged axially between said first and second distal ends of said electrodes and has a diameter which is substantially the same as a diameter of said electrodes at their distal ends.

3. A cutting device according to claim 1, wherein at least one of the lengths of said first and second elongated distal leg segments portions and the diameters of said first and second elongated distal leg segments portions differ for each leg segment.

4. A cutting device according to claim 1, wherein said two electrodes and said insulation element together form a loop.

5. A cutting device according to claim 1, wherein said electrodes are attached to said carrier element along a portion of their length.

6. A cutting device according to claim 1, wherein said carrier element is spatula-shaped and has two side edges and a cutting edge, wherein each of said first and second proximal portions are attached to respective said side edges of said carrier element, and said elongated distal leg portions are attached to said cutting edge of said carrier element.

7. A cutting device according to claim 5, wherein said carrier element has a hollow channel terminating in an opening for at least one of supplying a stream of rinsing material and supplying suction of body substances.

8. A cutting device according to claim 7, wherein said carrier element has a shaft surrounded by a sleeve, wherein an interior diameter of said sleeve is adapted to fit with an outer diameter of said shaft, so that said sleeve can be moved axially to focus at least one of the stream of the rinsing material and the suction of body substances.

9. A cutting device according to claim 5, further comprising a mounting part mechanically and electrically connected to said carrier element by a releasable plug-in connection.

10. A cutting device according to claim 1, wherein said insulation element comprises a ceramic material.

11. A cutting device for use in electrotomy with a high frequency generator, the cutting device comprising:

- a carrier element;
- a first electrode adapted to be connected to the high frequency generator and having a first proximal portion attached to said carrier element and a first elongated distal leg portion terminating in a first distal end;
- a second electrode adapted to be connected to the high frequency generator and having a second proximal portion attached to said carrier element and a second elongated distal leg portion terminating in a second distal end;
- an insulation element connecting said distal ends to each other with a predetermined spacing therebetween;
- a mounting part mechanically and electrically connected to said carrier element by a releasable plug-in connection, said plug-in connection comprising a saddle piece and a reception element adapted to fit said saddle piece; and
- a sleeve surrounding said mounting part and adapted to be moved in an axial direction relative to said saddle piece and said reception element to secure the plug-in connection.

* * * * *